United States Patent [19]

Fowee et al.

[11] Patent Number: 5,714,387
[45] Date of Patent: Feb. 3, 1998

[54] TRACER TECHNOLOGY FOR DUST CONTROL

[75] Inventors: Roger W. Fowee, Wheaton; J. David Martin, Elburn; Everett C. Phillips, Batavia, all of Ill.

[73] Assignee: Nalco Chemical Company, Naperville, Ill.

[21] Appl. No.: 608,226

[22] Filed: Feb. 28, 1996

Related U.S. Application Data

[63] Continuation-in-part of Ser. No. 362,370, Dec. 22, 1994, abandoned.

[51] Int. Cl.⁶ .................................................. G01N 21/64
[52] U.S. Cl. ......................... 436/27; 436/20; 436/172
[58] Field of Search ............................ 436/27, 172, 20

[56] References Cited

U.S. PATENT DOCUMENTS

| | | | |
|---|---|---|---|
| 4,300,908 | 11/1981 | Kugel | 23/230 R |
| 4,347,125 | 8/1982 | Di Giacomo | 209/3.3 |
| 4,487,615 | 12/1984 | Taylor et al. | 55/84 |
| 4,528,069 | 7/1985 | DuBroff et al. | 201/20 |
| 4,594,268 | 6/1986 | Kirwin | 427/136 |
| 4,666,741 | 5/1987 | Roe | 427/220 |
| 4,746,543 | 5/1988 | Zinkan et al. | 427/136 |
| 4,780,233 | 10/1988 | Roe | 252/88 |
| 4,801,635 | 1/1989 | Zinkman et al. | 524/156 |
| 5,024,753 | 6/1991 | Chriswell et al. | 209/1 |
| 5,181,957 | 1/1993 | Gross et al. | 75/772 |
| 5,215,784 | 6/1993 | Tippett et al. | |
| 5,396,075 | 3/1995 | Kaufman | 250/459.1 |
| 5,439,608 | 8/1995 | Kondrats | 252/88 |

*Primary Examiner*—Robert J. Warden
*Assistant Examiner*—Sharidan Carrillo
*Attorney, Agent, or Firm*—Robert A. Miller; James J. Drake

[57] ABSTRACT

A method of determining the dosage of dust control agents applied to coal is disclosed. The method comprises the steps of: (1) treating the coal, with a small amount of a dust control agent containing a compatible fluorescent dye; (2) extracting the treated coal with a polar solvent for the freeze-release agent and determining the fluorescence of such extract; (3) extracting a similar treated coal sample to which a known amount of the dust control agent has been further added and determining the fluorescence of this extract; (4) setting up a proportionality between the fluorescence values of extracts (2) and (3) with the corresponding dosages of dust control agents and solving for the unknown dosage originally applied to the coal.

3 Claims, 1 Drawing Sheet

TRACER TECHNOLOGY FOR DUST CONTROL

REFERENCE TO RELATED PATENTS

The present application is a continuation-in-part of application Ser. No. 08/362,370, filed Dec. 22, 1994, now abandoned by J. David Martin, Roger W. Fowee and Everett C. Phillips, entitled "Tracer Technology for Dust Control", the disclosure of which is incorporated herein by reference.

BACKGROUND OF THE INVENTION

1. Field of the Invention

The invention relates to the use of a fluorescent tracer molecule, such as an organic dye material or a fluorescent brightener, to aid in the monitoring, optimization, and the control of chemical agents used to prevent and/or suppress dust formation.

2. Description of the Prior Art

Chemical dust control agents such as surfactants and/or polymers are used to treat a variety of solid materials such as coals, lignite and clays to prevent and/or to suppress dust generated during the transport, stock-piling, sizing, crushing, dumping, and belt-to-belt transfers of the materials. Currently there are no diagnostic tools available to accurately confirm the dosage of the product, to aid in treatment system design and application, or to optimize and verify the performance of the chemical treatment program. Technology involving tracers in water systems such as cooling and boiler systems to measure system volume, determine cycles of concentration, and to control the application and dosage of treatment chemicals have been successfully used in the past.

Dust control products are typically applied to coal at 0.1–1 lb/ton levels using 1–3% solutions in water. Currently, product dosages are estimated from total volume gauges or flow rates of water and product used. In many cases, chemical treatment is applied to a free falling column of coal or sprayed on top of a pile. The actual dosage is difficult to accurately ascertain since the flow rate of the coal may vary and/or the actual amount of coal being treated is not known. As a result, it is very difficult to compare the effects of small changes in treatment dosages and to be certain of differences in one chemical program over another.

In most cases, the performance of the dust control chemical will depend on the adequate contact of the product with the coal and/or the penetration of the product into the coal being treated. For example, chemical treatments are applied to coal and filled rail cars to generate a crust on the surface. This crust reduces moisture loss from the coal and physical loss of surface coal from wind or rain or during transport over the rail (OTR). The crust thickness and strength is very important and will greatly depend on the amount of chemical applied and the penetration of the product. Usually, measurement of penetration involves waiting for the crust to dry, removing a portion of the crust and measuring the thickness of the crust with a ruler. This procedure takes time and changes cannot be made during treatment.

Another aspect with respect to the treatment of coal loaded in rail cars. Is the way that the coal is loaded into a rail car. Three major types of treatment/surface zones result: (a) two highly sloped areas at the front and back of the car; (b) a flat section on the top and center of the car: and (c) two small slopes at the sides of the car along the top portion. The dust control product is applied using a spray boom. The shape of the boom, the number of nozzles, the nozzle size(s) and their orientation and height with respect to the coal, will all affect how the product is applied and the amount applied to each area of the coal surface.

Desirably, a tracer having applications in the area of dust control, e.g. for mineral mining, coal, gravel/dirt road dust, etc., would exist. This would provide a much needed diagnostic tool to accurately confirm dosages of products, to aid in the design of treatment systems, and, to verify and optimize the performance of chemical treatment programs.

SUMMARY OF THE INVENTION

A method of determining the dosage of dust control agents applied to coal is disclosed. The method comprises the steps of: (1) treating the coal, with a small amount of a dust control agent containing a compatible fluorescent dye; (2) extracting the treated coal with a polar solvent for the freeze-release agent and determining the fluorescence of such extract; (3) extracting a similar treated coal sample to which a known amount of the dust control agent has been further added and determining the fluorescence of this extract; (4) setting up a proportionality between the fluorescence values of extracts (2) and (3) with the corresponding dosages of dust control agents and solving for the unknown dosage originally applied to the coal.

DESCRIPTION OF THE PREFERRED EMBODIMENTS

Figure 1:
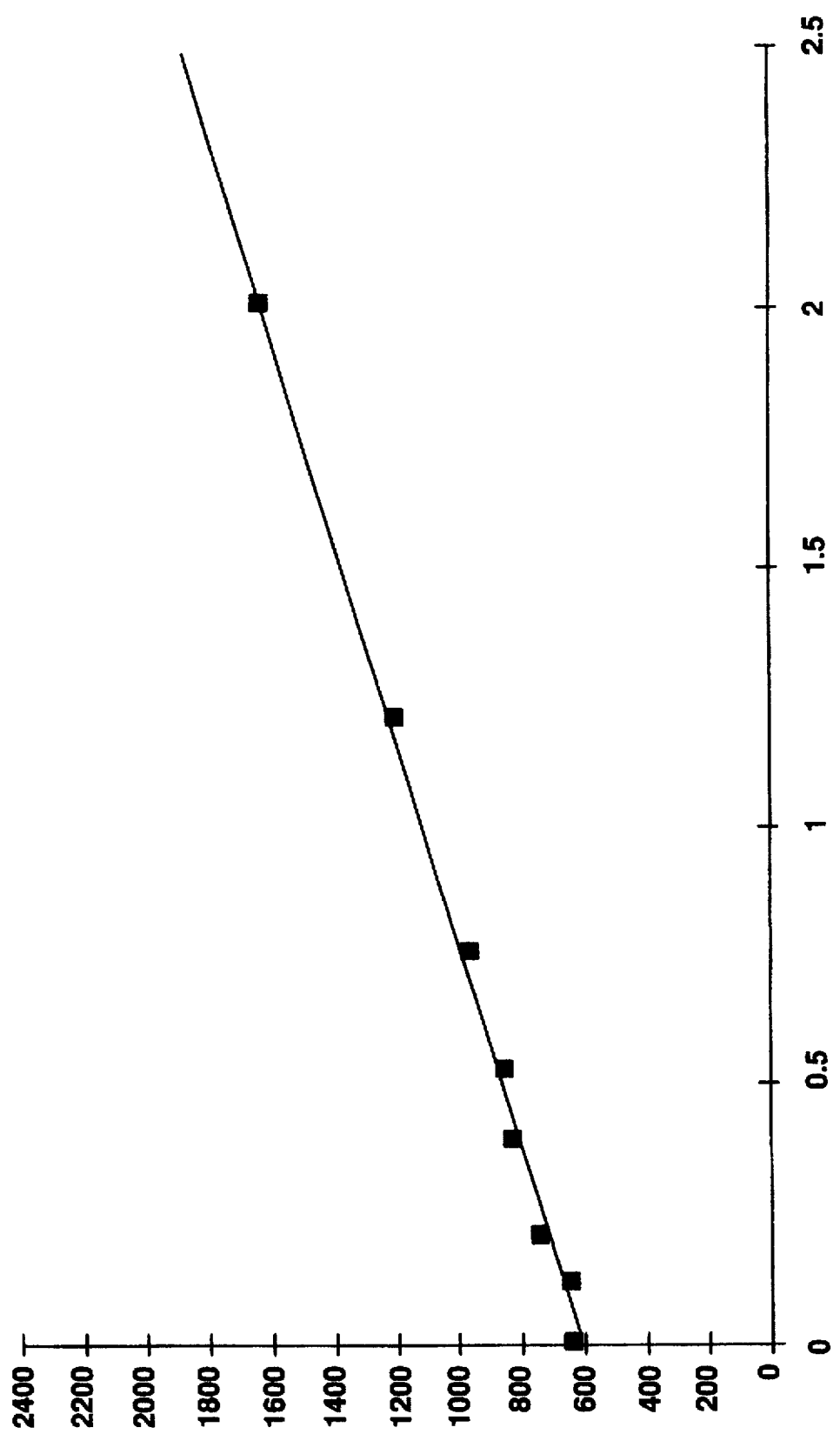
FIG. 1 is a calibration fluorescence curve for a dust control product.

The invention comprises a method of determining the dosage of freeze-dust suppressant conditioning agents applied to coal. The tracer agent is preferably selected from any of the following:

| Name | Chemical Type | Supplier |
| --- | --- | --- |
| D & C Green 8 | pyrene | Hilton-Davis Chemical |
| Solvent Green 7 | pyrene | AAKASH Chemicals & Dye Stuffs |
| Acid yellow 73 (A.K.A. Fluorescein) | xanthene | Plyam |
| Basic Violet 10 (A.K.A. Rhodamine B) | xanthene | |

In another embodiment, the tracer is used in conjunction with a dust control product selected from the following group:

Residual Dust Control Products—applications to coal handling, sizing, storage.

| Product | Components |
| --- | --- |
| N1276 | ethoxylated nonyl phenol - surfactant |
| N1277 | ethoxylated nonyl phenol - surfactant |
| N1293 | tall oil, ethoxylated nonyl phenol superadsorbent, antifoam |
| N1295 | oil, tall oil, surfactant |
| N7977 | surfactants - glycol, ethoxylated nonyl phenol and lignosulfonate |

Over-the-Rail Topper/Dust Control Products—mainly used for loading and shipment of coal from mine to utility.

| Product | Components |
| --- | --- |
| N7823 | ethoxylated-N-alcohol, tween, and acrylate/acrylamide copolymer |
| N7826 | ethoxylated-N-alcohol, tween, and acrylate/acrylamide polymer |
| N9832 | ethoxylated-N-alcohol, tween, and acrylate/acrylamide polymer |

The method comprises treating the coal with a small amount of a dust suppressant agent containing a compatible fluorescent tracer dye. Preferably, the dye is selected from Acid Yellow 73 or Basic Violet.

Preferably, the dye is added to the dust control at a dosage of between 0.001% to 1% tracer based on the weight of the dust control agent. More preferably, the dosage is from 0.05% to 0.75% based on the weight of the dust control agent. Most preferably the dosage is from 0.15% to 0.5% based on the weight of the dust control agent.

There are numerous fluorescent tracers which are capable of equivalent performances as substitutes for 2-naphthalenesulfonic acid or Acid Yellow 73, and whose concentration may be quantitatively measured at trace levels ranging from parts per trillion (ppt) to parts per million (ppm). Those fluorescent tracers may be soluble in water, organic solvents, inorganic solvents or mixtures of solvents chosen from one or more of the classes of liquids described. Those tracers may also be chosen from classes of materials which are excited by absorption of light and produce fluorescent light emission, where the excitation and emission light occurs at any point within the far ultraviolet to near infrared spectral regions (wavelengths from 200–800 nm). Preferably, the fluorescent material of the invention is a compound having yellow to green visible fluourscence or blue-white visible fluorescence. Combinations of one or more fluorescent tracers may also be used combination with other fluorescent materials as long as the absorption of excitation light and emission of fluorescent light from the other components does not interfere with detection of light emission from the fluorescent tracers.

Once the coal has been treated, it is extracted with a solvent for the freeze-release agent. Preferable solvents include polar solvents such as alcohols and alcohol-water mixtures. More preferably the solvents may be selected from among ethanol, propanol and acetone.

After application of the solvent, the fluorescence of the resulting extract is determined. The concentration of tracer is then determined from a calibration curve of tracer concentration versus emission. That comparison permits the determination of the concentration range over which linear emission response is observed. At higher tracer concentrations, a negative deviation from ideal behavior is observed. The concentration of the tracer can still be determined directly from the calibration curve or the sample can be diluted until the tracer concentration falls within the linear emission response range.

By properly choosing the fluorescing reagent, quantitative and in situ measurement of tracer levels from parts per trillion (ppt) to parts per million (ppm) can be routinely accomplished on an instant or continuous basis with inexpensive portable equipment. In addition, multiple tracers may be used concurrently by choice of tracers with proper spectral characteristics. As such, various combinations of fluorescent tracers and treatment feeds can be quantified. For example, four individual treatments containing a single unique fluorescent tracer plus one additional treatment containing the two fluorescent tracers could be employed within a given system. In that case, each fluorescent tracer and the corresponding individual concentration of the five treatments can each be quantified. In addition to being able to quantify complex combinations of the treatments, fluorescent compounds are available which are environmentally acceptable, are not degraded by or deposited within the liquid systems, and are available at low cost. The invention can generally be applied in the following ways:

(a) direct addition of from one or more fluorescent tracers to a the system being treated;

(b) incorporation of one to six (or even more) fluorescent tracers into chemical treatment composition containing other components and said treatment is applied to the system in order to maintain proper operation of that system;

(c) addition of one to six chemical treatment agents (or even more) containing fluorescent tracer(s) directly into the system or into the feed leading into system;

(d) addition of fluorescent tracers so that within the liquid system individual tracer concentrations ranging from 1 part per trillion to 100 parts per million (ppm), preferably from 1 part per billion (ppb) to 10 ppm, and most preferably from 10 ppb to 2 ppm are realized.

Subsequent to the addition of the tracer, a coal sample to which a known amount of the dust control agent has been further added is extracted, and analyzed to determine the fluorescence of the second extract. Finally, a proportionality is set up between the fluorescence values of the first extract and the second extract with the corresponding dosages of dust control agents and solving for the unknown dosage originally applied to the coal.

Incorporating a known amount of a fluorescent tracer into the product and the use of on-line measurement of the amount of fluorescence (directly related to product concentration), allows continuous monitoring of product dosage and variation, allows easy adjustment of product dosage and provides more effective control over the application of the product. Additionally, the actual dust control product dosage applied to the coal can also be quantified by using an extraction method to remove the fluorescent tracer from a specified quantity of coal and measure the solution fluorescence against standard solutions of the tracer.

A number of measurement techniques are available to compare extracts. For tracers which fluoresce in the visible range of the spectrum, a Black-Light or Ultra-Violet lamp is preferably used to quickly assess the amount of penetration of the product and the coverage of the product on the surface of the coal. The major benefit of this method is the ability to quickly change product and water dosages to optimize product penetration and the crust thickness. Depending on the type of treatment, various penetration levels may be desired, for instance treatments involving surfactants which allow better wetting of the coal versus polymer treatments for crust formation.

The tracer can be used as a diagnostic tool to optimize how products are applied to the coal, which will help in the proper design of the treatment system. For example, optimization of the spray boom configuration and nozzle type and/or alignment. Using a hand held UV-lamp the surface of the treated coal can be scanned for the visible fluorescence of the tracer, to inspect uniformity in the product application, and to identify areas of over-treatment and/or under-treatment.

Using a UV lamp to scan for the visible fluorescence of the tracer will identify areas of over-treatment and under-treatment and this will allow for the optimization of the spray system and achieve optimum product dosages over all surfaces. A similar method may be used for spraying coal piles. Identifying areas where the products are oversprayed or lost can help save product use and treatment costs. An example of this is the potential for channeling of treatment chemicals into the coal bed or pile at the sides of the rail car because of very coarse loosely packed surfaces. This results in the loss of the chemical from the surface where crust formation is desired.

An additional application area exists for visual inspection of the coverage of treatment chemicals when they are applied to free falling coal during handling at belt-to-belt transfer points. Use of a tracer will optimize the treatment system, chemical dose and ensure the best performance of our products.

Crust formation is desirable for the minimization of moisture loss from coal. Minimizing moisture loss is important to minimize the amount of dust generated when the coal is dumped at its destination point. The tracer can be used to evaluate the amount of coal lost during transport by treating a coal-filled rail car with only water containing a known concentration of the tracer. The tracer concentration is such that when applied it is easily visible with the use of a hand held UV lamp which can determine the relative concentration of applied tracer from the intensity of the fluorescence compared to standard strips of known concentration of the tracer on solid substrates. A second coal car is treated with the same amount of water and tracer, but, it is also sealed with the a conventional sealant to form a crust on the surface. Penetration of the tracer into both coal beds can easily be evaluated at several grid points on the coal surface along the length of the cars. The depth of the tracer at the same grid points in each of the cars is further evaluated at the destination point after OTR transport. Loss in tracer/crust thickness corresponds to loss of coal from the rail car. Knowing the initial and final trace depths in both cars and the surface area of the coal treated in both cases will provide the amount of coal lost with and without chemical treatment. The result will demonstrate the performance of the product/ treatment. A tracer with high fastness to sunlight and rain is required for such a test to ensure that the tracer does not photodegrade or is not washed or lost into the bed during the transport. Preferably, the tracer to be used in this application would be Cartax CXDP powder or DP Liquid.

Fluorescence emission in the system is measured either continuously or by grab samples, the fluorescence intensity is proportional to product concentration. Results are compared to a calibration curve of the fluorescence versus the concentration of product at various dilutions.

EXAMPLE 1

In FIG. 1, the calibration fluorescence curve for a dust control product (Product A) traced with 10 ppm of Acid Yellow 73 is shown at various dilutions from 0.1 to 2.0% product solutions. Dust control products are typically applied at a dosage of from 0.1–1 lb/ton of coal using 1 to 3% solutions. The product to be traced with fluorescent compound will preferably be detected at dosages of between 100 ppb to 1%, more preferably 2 ppm to 200 ppm and most preferably between 5 and 65 ppm.

Product A was traced with Fluorescein at 10 ppm by adding 0.0025 g of a 40% Fluorescein solution to 99.99 g of the product. A series of dilutions of the traced product at 0.19%, 0.2%, 0.4%, 0.5%, 0.75%, 1% and 2% were prepared and the fluorescence measured. FIG. 1 shows a linear curve for this range. The fluorescence of these solutions was measured using a surface fluorescence cell because the samples have sufficient turbidity that light cannot pass through the sample.

In another embodiment of the invention, a tracer is used to determine the actual base of the treatment chemical applied to the coal being treated. This method is outlined in U.S. Pat. No. 4,300,908, the disclosure of which is incorporated herein by reference.

Still another embodiment of the invention comprises utilizing the tracer to measure product penetration and product performance. The following example outlines how the determination is made.

EXAMPLE 2

Laboratory test using a variety of containers or trays was used to simulate a pile of coal in a mine or utility stockyard or a pile of coal in a rail car. In a "real system", coal pile height and diameter varies greatly. Normally, a rail car is approximately 50' long by 10' wide, producing a pile of coal having a surface area of 500 ft$^2$.

| Models used | Dimensions | Scale* |
|---|---|---|
| I.) 2.5 gal round bucket | 10.75" l × 8" h | 1/757.6 |
| II) plexiglass cube | 7.5" l × 8.5" w × 10" h | 1/1136 |
| III) aluminum pan | 11.5" l × 9" w × 2.5" h | 1/675.7 |

*Scale = surface area of rail car with respect to surface area of model container Equipment An internally designed spray system that mimics actual spray equipment employed in field was used. For the case of over-the-rail applications, a system consisting of chemical feed tanks (5–50 gal), variable speed pump, flood jet type spray nozzles was used. Test cars were mounted on a track system with a pulley. A motor drives the pulley to simulate the loading and spraying of a slow moving (1–3 mph) train.

Product Treatment and Dose

The type of program and dose will depend on coal type, moisture content, dustiness and particle size distribution. For so-called topper applications in over-the-raft treatments surfactants and/or polymers such as polyacrylate and polyacrylamide copolymer are used. Typically, 0.5–3% product solutions at 30 to 150 gallons of solution per car are indicated.

First, the ability to spray various tracers onto the coal surface and detect visible fluorescence using a hand held black light (short wave UV) was tested. Also, tracer light fastness and water fastness must be determined in order to accurately measure values and make comparisons. A small aluminum pan having 1/1515 surface area of a typical rail car was used for the laboratory test. The conversion factors for the amount of coal used were 250 g=0.55 lb=2.75×10$^{-4}$ tons. The following Table summarizes the results of the test.

| Tracer Used | Solution Strength | Dosage lbs/lbs | % solids |
|---|---|---|---|
| D&C Green 8 | 2.5% | 1.4 × 10$^{-4}$ | 0.014 |
| Day-Glo Signal Green | 1.7% | 1.2 × 10$^{-3}$ | 0.12 |
| Day-Glo blaze Orange | 1.1% | 1.36 × 10$^{-4}$ | 0.014 |
| Leucopure EGM F.B. 236 | 1.0% | 2.0 × 10$^{-4}$ | 0.02 |
| Cartax DP Liquid* | 3% | 1.9 × 10$^{-5}$–5 × 10$^{-4}$ | 0.002–0.05 |

*Commercially available yet proprietary oxazinone dye compound. Many other fluorescent brighteners tested but only those above gave excellent light fastness and water fastness that were desired.

Once sprayability was determined to be adequate, testing of product penetration was carded out using Nalco® N7826 traced with Cartax DP Liquid ( a 30% dispersion of a dye in aqueous surfactant). Table II below shows the results of this test. After topper treatments were allowed to dry for 6–12 hours a black light was used to inspect core samples from the coal bed to determine the extent of product penetration.

A core sampler was used to remove a 6" to 2' core sample from the top of the coal bed. The core is then removed and laid horizontally. The black light can identify the distance traveled down from the top of the bed. The point where visible fluorescence is no longer evident is then measured to determine product penetration.

In another embodiment of the invention, a tracer is used to optimize product application and system design. In this application, tracer levels are such that fluorescence of a treatment solution may be visually observed. In this case, the tracer concentration is preferably measured at at least 100 ppb and is at a maximum of up to 4% of the total weight of the aqueous solution. More preferably, the tracer concentration is measured at at least 400 ppb and is at a maximum of up to 1%. Most preferably, the tracer concentration is measured at at least 500 ppb and is at a maximum of up to 1.5 ppm. Preferred tracers include Fluorescein, Rhodamine, and Cartax.

Yet another embodiment of the invention is a method of evaluating over-the-rail loss during transport of coal and other products. Preferably, the tracer used is Cartax DP Liquid manufactured by Sandoz Chemicals. In this embodiment, the tracer is applied to both cars using a preferred dispersion of the tracer in water at 0.0001 to 4% concentration by weight. More preferably, the concentration is at 0.005% to 3% by weight. Most preferably the concentration is at 0.25% to 1% by weight.

A second car (B) is then treated with treatment chemical to form crust on the surface of the second car. Core samples from both cars were then removed to evaluate an average tracer depth. After transport from the mine to the utility several core samples from both cars are taken to re-evaluate tracer depth. These results can help provide valuable information on the performances of our program and an estimate of the coal lost from the surface of the car (B) if left untreated. No loss can be detected from the front and back sections. However the fraction of the car can be measured. For example in a 35 ft by 10 ft car at 70% of full capacity, the coal in the car will be 0.7×110 tons=77 tons and loss of 3% from this section, i.e., 2.3 tons.

TABLE III

| Number | Car # | Time (days) | Distance (miles) | Tracer Depth | | |
|---|---|---|---|---|---|---|
| | | | | Font (in) | Top (in) | Back (in) |
| 1 | (a) | 0 | 0 | 6.4 ± 2 | 6.4 ± 2 | 6.4 ± 2 |
| 2 | (b) | 0 | 0 | 6.6 ± 2 | 6.6 ± 2 | 6.6 ± 2 |
| 3 | (a) | 5 | 2100 | 6.5 ± 2 | 2.5 ± 2 | 6.5 ± 2 |
| 4 | (b) | 5 | 2100 | 6.6 ± 2 | 5.9 ± 2 | 6.2 ± 2 |

Changes can be made in the composition, operation and arrangement of the method of the present invention described herein without departing from the concept and scope of the invention as defined in the following claims:

We claim:

1. A method for maximizing contact of spray dust control products on coal, comprising;

a) providing a source of coal;

b) incorporating a known concentration of fluorescent material, the fluorescent material having yellow to green visible fluorescence, into a dust control product;

c) spraying the coal with a mixture of water and the dust control product containing the fluorescent material;

d) detecting visible fluorescence on the sprayed coal with an ultraviolet lamp;

e) using the visible fluorescence to determine an extent and uniformity of spray coverage on the coal and to identify surface areas of the coal which have been over-sprayed or under-sprayed with the dust control product; and f) modifying spray equipment to ensure maximum contact over all surface areas of the coal in response to the over-sprayed or under-sprayed surface areas.

2. The method of claim 1, wherein the fluorescent material is a brightener having blue-white visible fluorescence.

3. The method of claim 1, wherein a relative concentration of the fluorescent material is determined from a comparison made between the visible fluorescence detected by the ultraviolet lamp and standard strips having known concentrations of the fluorescent material.

\* \* \* \* \*